United States Patent
Chang et al.

(10) Patent No.: US 11,737,920 B2
(45) Date of Patent: Aug. 29, 2023

(54) ADJUSTABLE FLOW GLAUCOMA SHUNTS HAVING NON-LINEARLY ARRANGED FLOW CONTROL ELEMENTS, AND ASSOCIATED SYSTEMS AND METHODS

(71) Applicant: Shifamed Holdings, LLC, Campbell, CA (US)

(72) Inventors: Robert Chang, Belmont, CA (US); Claudio Argento, Felton, CA (US); Katherine Sapozhnikov, Campbell, CA (US); Tom Saul, Moss Beach, CA (US); Richard Lilly, San Jose, CA (US)

(73) Assignee: Shifamed Holdings, LLC, Campbell, CA (US)

(*) Notice: Subject to any disclaimer, the term of this patent is extended or adjusted under 35 U.S.C. 154(b) by 0 days.

(21) Appl. No.: 17/798,811

(22) PCT Filed: Feb. 18, 2021

(86) PCT No.: PCT/US2021/018601
§ 371 (c)(1),
(2) Date: Aug. 10, 2022

(87) PCT Pub. No.: WO2021/168130
PCT Pub. Date: Aug. 26, 2021

(65) Prior Publication Data
US 2023/0086856 A1    Mar. 23, 2023

Related U.S. Application Data

(60) Provisional application No. 62/978,210, filed on Feb. 18, 2020, provisional application No. 63/018,393, filed on Apr. 30, 2020.

(51) Int. Cl.
*A61F 9/007* (2006.01)
*B21D 53/00* (2006.01)

(52) U.S. Cl.
CPC .......... *A61F 9/00781* (2013.01); *B21D 53/00* (2013.01); *A61F 2210/0014* (2013.01);
(Continued)

(58) Field of Classification Search
CPC ................. A61F 9/00781; B21D 53/00; Y10T 29/49936
See application file for complete search history.

(56) References Cited

U.S. PATENT DOCUMENTS

| 4,401,107 A | 8/1983 | Harber et al. |
| 4,595,390 A | 6/1986 | Hakim et al. |

(Continued)

FOREIGN PATENT DOCUMENTS

| AU | 2014201621 B2 | 3/2016 |
| AU | 2016201445 B2 | 3/2016 |

(Continued)

OTHER PUBLICATIONS

International Search Report and Written Opinion received for PCT Application No. PCT/US22/37917, filed on Jul. 21, 2022, Applicant: Shifamed Holdings, LLC, dated Dec. 15, 2022, 15 pages.
(Continued)

*Primary Examiner* — Jermie E Cozart
(74) *Attorney, Agent, or Firm* — Perkins Coie LLP (57) ABSTRACT

In particular, some embodiments provide shunts having a plurality of individually actuatable flow control elements that can control the flow of fluid through associated ports and/or flow lumens. For example, each individually actuatable flow control element can be actuated to modify a flow of a corresponding port and/or flow lumen. The individually actuatable flow control elements may be actuated along a given actuation axis. A flow control assembly may include a plurality of flow control elements arranged about a collection region. Accordingly, the shunts described herein can be manipulated into a variety of configurations that provide
(Continued)

different drainage rates based on a degree to which the ports and/or flow lumens are blocked or unblocked, therefore providing a titratable glaucoma therapy for draining aqueous from the anterior chamber of the eye.

9 Claims, 6 Drawing Sheets

(52) U.S. Cl.
CPC .............. *A61F 2220/0033* (2013.01); *A61F 2240/001* (2013.01); *A61F 2250/0003* (2013.01); *A61F 2250/0013* (2013.01); *Y10T 29/49936* (2015.01)

(56) References Cited

U.S. PATENT DOCUMENTS

| | | |
|---|---|---|
| 5,070,697 A | 12/1991 | Van Zeggeren |
| 5,123,906 A | 6/1992 | Kelman |
| 5,476,445 A | 12/1995 | Baerveldt et al. |
| 5,601,094 A | 2/1997 | Reiss |
| 6,077,298 A | 6/2000 | Tu et al. |
| 6,077,299 A | 6/2000 | Adelberg et al. |
| 6,203,513 B1 | 3/2001 | Yaron et al. |
| 6,261,256 B1 | 7/2001 | Ahmed |
| 6,450,984 B1 | 9/2002 | Lynch et al. |
| 6,508,779 B1 | 1/2003 | Suson |
| 6,626,858 B2 | 9/2003 | Lynch et al. |
| 6,633,239 B2 | 10/2003 | Bergheim et al. |
| 6,666,841 B2 | 12/2003 | Gharib et al. |
| 6,736,791 B1 | 5/2004 | Tu et al. |
| 6,789,447 B1 | 9/2004 | Zinck |
| 7,025,740 B2 | 4/2006 | Ahmed |
| 7,207,965 B2 | 4/2007 | Simon |
| 7,354,416 B2 | 4/2008 | Quiroz-Mereado et al. |
| 7,458,953 B2 | 12/2008 | Peyman |
| 7,699,882 B2 | 4/2010 | Stamper et al. |
| 7,717,872 B2 | 5/2010 | Shetty |
| 7,947,008 B2 | 5/2011 | Grahn et al. |
| 8,012,134 B2 | 9/2011 | Claude et al. |
| 8,206,333 B2 | 6/2012 | Schmidt et al. |
| 8,206,440 B2 | 6/2012 | Guarnieri |
| 8,298,240 B2 | 10/2012 | Giger et al. |
| 8,308,701 B2 | 11/2012 | Horvath et al. |
| 8,414,635 B2 | 4/2013 | Hyodoh et al. |
| 8,506,515 B2 | 8/2013 | Burns et al. |
| 8,540,659 B2 | 9/2013 | Berlin |
| 8,579,848 B2 | 11/2013 | Field et al. |
| 8,585,629 B2 | 11/2013 | Grabner et al. |
| 8,663,303 B2 | 3/2014 | Horvath et al. |
| 8,702,639 B2 | 4/2014 | Van Der Mooren et al. |
| 8,721,702 B2 | 5/2014 | Romoda et al. |
| 8,753,305 B2 | 6/2014 | Field et al. |
| 8,758,290 B2 | 6/2014 | Horvath et al. |
| 8,765,210 B2 | 7/2014 | Rornoda et al. |
| 8,771,220 B2 | 7/2014 | Nissan et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,882,781 B2 | 11/2014 | Smedley et al. |
| 8,915,877 B2 | 12/2014 | Cunningham et al. |
| 8,974,511 B2 | 3/2015 | Horvath et al. |
| 9,017,276 B2 | 4/2015 | Horvath et al. |
| 9,095,411 B2 | 8/2015 | Horvath et al. |
| 9,095,413 B2 | 8/2015 | Romoda et al. |
| 9,113,994 B2 | 8/2015 | Horvath et al. |
| 9,125,723 B2 | 9/2015 | Horvath et al. |
| 9,192,516 B2 | 11/2015 | Horvath et al. |
| 9,226,851 B2 | 1/2016 | Gunn |
| 9,271,869 B2 | 3/2016 | Horvath et al. |
| 9,283,115 B2 | 3/2016 | Lind et al. |
| 9,283,116 B2 | 3/2016 | Rornoda et al. |
| 9,289,324 B2 | 3/2016 | Johnson et al. |
| 9,326,891 B2 | 5/2016 | Horvath et al. |
| 9,375,347 B2 | 6/2016 | Stergiopulos |
| 9,393,153 B2 | 7/2016 | Horvath et al. |
| 9,555,410 B2 | 1/2017 | Brammer et al. |
| 9,585,789 B2 | 3/2017 | Silvestrini et al. |
| 9,585,790 B2 | 3/2017 | Horvath et al. |
| 9,592,154 B2 | 3/2017 | Romoda et al. |
| 9,610,195 B2 | 4/2017 | Horvath |
| 9,636,254 B2 | 5/2017 | Yu et al. |
| 9,655,778 B2 | 5/2017 | Tyler |
| 9,655,779 B2 | 5/2017 | Bigler et al. |
| 9,693,900 B2 | 7/2017 | Gallardo Inzunza |
| 9,693,901 B2 | 7/2017 | Horvath et al. |
| 9,757,276 B2 | 9/2017 | Penhasi |
| 9,808,373 B2 | 11/2017 | Horvath et al. |
| 9,877,866 B2 | 1/2018 | Horvath et al. |
| 9,883,969 B2 | 2/2018 | Horvath et al. |
| 9,980,854 B2 | 5/2018 | Horvath et al. |
| 10,004,638 B2 | 6/2018 | Romoda et al. |
| 10,080,682 B2 | 9/2018 | Horvath et al. |
| 10,085,884 B2 | 10/2018 | Reitsamer et al. |
| 10,154,924 B2 | 12/2018 | Clauson et al. |
| 10,159,600 B2 | 12/2018 | Horvath et al. |
| 10,195,078 B2 | 2/2019 | Horvath et al. |
| 10,195,079 B2 | 2/2019 | Horvath et al. |
| 10,231,871 B2 | 3/2019 | Hill |
| 10,238,536 B2 | 3/2019 | Olson et al. |
| 10,285,853 B2 | 5/2019 | Rangel-Friedman et al. |
| 10,307,293 B2 | 6/2019 | Horvath et al. |
| 10,314,743 B2 | 6/2019 | Romoda et al. |
| 10,322,267 B2 | 6/2019 | Hakim |
| 10,335,030 B2 | 7/2019 | Alhourani |
| 10,369,048 B2 | 8/2019 | Horvath et al. |
| 10,405,903 B1 | 9/2019 | Biesinger et al. |
| 10,342,703 B2 | 11/2019 | Siewert et al. |
| 10,463,537 B2 | 11/2019 | Horvath et al. |
| 10,470,927 B2 | 11/2019 | Horvath et al. |
| 10,363,168 B2 | 12/2019 | Schieber et al. |
| 10,492,948 B2 | 12/2019 | Baerveldt |
| 10,524,958 B2 | 1/2020 | Camras et al. |
| 10,524,959 B2 | 1/2020 | Horvath |
| 10,596,035 B2 | 4/2020 | Stergiopulos et al. |
| 10,753,412 B2 | 4/2020 | Velasquez |
| 10,716,663 B2 | 7/2020 | Salahieh et al. |
| 11,122,975 B2 | 1/2021 | Rodger et al. |
| 10,912,675 B2 | 2/2021 | Lubatschowski |
| 10,952,897 B1 | 3/2021 | Smith |
| 10,960,074 B2 | 3/2021 | Berdahl |
| 11,007,061 B2 | 5/2021 | Passman et al. |
| 11,039,954 B2 | 6/2021 | Cohen et al. |
| 11,058,581 B2 | 7/2021 | Mixter et al. |
| 11,065,154 B1 | 7/2021 | Sponsel et al. |
| 11,083,624 B2 | 8/2021 | Stein et al. |
| 11,166,847 B2 | 11/2021 | Badawi et al. |
| 11,166,848 B2 | 11/2021 | Mixter et al. |
| 11,166,849 B2 | 11/2021 | Mixter et al. |
| 11,291,585 B2 | 4/2022 | Schultz et al. |
| 11,517,477 B2 | 12/2022 | Lilly et al. |
| 11,529,258 B2 | 12/2022 | Chang et al. |
| 11,596,550 B2 | 3/2023 | Chang et al. |
| 2001/0011535 A1 | 8/2001 | Cassidy et al. |
| 2002/0177891 A1 | 11/2002 | Miles et al. |
| 2002/0193725 A1 | 12/2002 | Odrich |
| 2003/0127090 A1 | 7/2003 | Gifford et al. |
| 2003/0163079 A1 | 8/2003 | Burnett |
| 2004/0010219 A1 | 1/2004 | McCusker et al. |
| 2004/0193095 A1 | 9/2004 | Shadduck |
| 2004/0254520 A1 | 12/2004 | Porteous et al. |
| 2005/0049578 A1 | 3/2005 | Tu et al. |
| 2006/0004317 A1 | 1/2006 | Mauge et al. |
| 2006/0069340 A1 | 3/2006 | Simon |
| 2006/0155300 A1 | 7/2006 | Stamper et al. |
| 2006/0276739 A1 | 12/2006 | Brown |
| 2007/0010837 A1 | 1/2007 | Tanaka |
| 2007/0078371 A1 | 4/2007 | Brown et al. |
| 2007/0088432 A1 | 4/2007 | Solovay et al. |
| 2007/0265646 A1 | 11/2007 | McCoy et al. |
| 2008/0077071 A1 | 3/2008 | Yaron et al. |

(56) References Cited

U.S. PATENT DOCUMENTS

| | | |
|---|---|---|
| 2008/0119891 A1 | 5/2008 | Miles et al. |
| 2008/0125691 A1 | 5/2008 | Yaron et al. |
| 2008/0277332 A1 | 11/2008 | Liu |
| 2009/0012483 A1 | 1/2009 | Blott et al. |
| 2009/0036818 A1 | 2/2009 | Grahn et al. |
| 2009/0243956 A1 | 10/2009 | Keilman et al. |
| 2009/0287136 A1 | 11/2009 | Castillejos |
| 2009/0314970 A1 | 12/2009 | McAvoy et al. |
| 2009/0326517 A1 | 12/2009 | Bork et al. |
| 2010/0114006 A1 | 5/2010 | Baerveldt |
| 2010/0234791 A1 | 9/2010 | Lynch et al. |
| 2010/0241077 A1 | 9/2010 | Geipel et al. |
| 2010/0249691 A1 | 9/2010 | Van Der Mooren et al. |
| 2011/0105986 A1 | 5/2011 | Bronstein et al. |
| 2012/0035525 A1 | 2/2012 | Silvestrini |
| 2012/0065570 A1 | 3/2012 | Yeung et al. |
| 2012/0089073 A1 | 4/2012 | Cunningham, Jr. |
| 2012/0232461 A1 | 9/2012 | Seaver et al. |
| 2013/0085440 A1 | 4/2013 | Bohm et al. |
| 2013/0131577 A1 | 5/2013 | Bronstein et al. |
| 2013/0150773 A1 | 6/2013 | Nissan et al. |
| 2013/0150776 A1 | 6/2013 | Bohm et al. |
| 2013/0158381 A1 | 6/2013 | Rickard |
| 2013/0197621 A1 | 8/2013 | Ryan et al. |
| 2013/0199646 A1 | 8/2013 | Brammer et al. |
| 2013/0205923 A1 | 8/2013 | Brammer et al. |
| 2013/0211312 A1 | 8/2013 | Geivin |
| 2013/0267887 A1 | 10/2013 | Kahook et al. |
| 2013/0317412 A1 | 11/2013 | Dacquay et al. |
| 2013/0338564 A1 | 12/2013 | Rickard et al. |
| 2014/0046439 A1 | 2/2014 | Dos Santos et al. |
| 2014/0081195 A1 | 3/2014 | Clauson et al. |
| 2014/0309611 A1 | 10/2014 | Wilt et al. |
| 2015/0011926 A1 | 1/2015 | Reitsamer et al. |
| 2015/0034217 A1 | 2/2015 | Vad |
| 2015/0045716 A1 | 2/2015 | Gallardo Inzunza |
| 2015/0142049 A1 | 5/2015 | Delgado et al. |
| 2015/0230843 A1 | 8/2015 | Palmer et al. |
| 2015/0313603 A1 | 11/2015 | Bodewadt et al. |
| 2016/0151179 A1 | 6/2016 | Favier et al. |
| 2016/0220794 A1 | 8/2016 | Negre |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0287439 A1 | 10/2016 | Stergiopulos |
| 2016/0354244 A1 | 12/2016 | Horvath et al. |
| 2016/0354245 A1 | 12/2016 | Horvath et al. |
| 2017/0027582 A1 | 2/2017 | Khoury et al. |
| 2017/0071791 A1 | 3/2017 | Piven |
| 2017/0087016 A1 | 3/2017 | Camras |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0312125 A1 | 11/2017 | Clauson et al. |
| 2017/0348149 A1 | 12/2017 | Stergiopulos et al. |
| 2017/0348150 A1 | 12/2017 | Horvath et al. |
| 2018/0014828 A1 | 1/2018 | Fonte et al. |
| 2018/0028361 A1 | 2/2018 | Haffner et al. |
| 2018/0028366 A1 | 2/2018 | Tout et al. |
| 2018/0092775 A1 | 4/2018 | de Juan, Jr. et al. |
| 2018/0147089 A1 | 5/2018 | Horvath et al. |
| 2018/0206878 A1 | 7/2018 | Uspenski et al. |
| 2018/0250166 A1 | 9/2018 | Lubatschowski |
| 2019/0000673 A1 | 1/2019 | Fjield et al. |
| 2019/0021907 A1 | 1/2019 | Horvath et al. |
| 2019/0038462 A1 | 2/2019 | Vandiest et al. |
| 2019/0046356 A1 | 2/2019 | Laroche |
| 2019/0060118 A1 | 2/2019 | Hill |
| 2019/0121278 A1 | 4/2019 | Kawamura et al. |
| 2019/0133826 A1 | 5/2019 | Horvath et al. |
| 2019/0142632 A1 | 5/2019 | Badawi et al. |
| 2019/0167475 A1 | 6/2019 | Horvath et al. |
| 2019/0240069 A1 | 8/2019 | Horvath et al. |
| 2019/0247231 A1 | 8/2019 | McClunan |
| 2019/0254873 A1 | 8/2019 | Camras et al. |
| 2019/0274881 A1 | 9/2019 | Romoda et al. |
| 2019/0274882 A1 | 9/2019 | Romoda et al. |
| 2019/0307608 A1 | 10/2019 | Lee et al. |
| 2019/0344057 A1 | 11/2019 | Cima et al. |
| 2019/0350758 A1 | 11/2019 | Horvath et al. |
| 2019/0353269 A1 | 11/2019 | Ossmer et al. |
| 2019/0358086 A1 | 11/2019 | Camras et al. |
| 2019/0374384 A1 | 12/2019 | Xle et al. |
| 2020/0069469 A1 | 3/2020 | Horvath et al. |
| 2020/0085620 A1 | 3/2020 | Euteneuer et al. |
| 2020/0121503 A1 | 4/2020 | Badawi et al. |
| 2020/0121504 A1 | 4/2020 | Stegmann et al. |
| 2020/0129332 A1 | 4/2020 | Van Der Mooren et al. |
| 2020/0170839 A1 | 6/2020 | Borrmann et al. |
| 2020/0179171 A1 | 6/2020 | Crimaldi et al. |
| 2020/0214891 A1 | 7/2020 | Bigler et al. |
| 2020/0229977 A1 | 7/2020 | Mixter et al. |
| 2020/0229980 A1 | 7/2020 | Horvath |
| 2020/0229981 A1 | 7/2020 | Mixter et al. |
| 2020/0229982 A1 | 7/2020 | Mixter et al. |
| 2020/0246188 A1 | 8/2020 | Horvath et al. |
| 2020/0261271 A1 | 8/2020 | Horvath et al. |
| 2020/0276050 A1 | 9/2020 | Simons et al. |
| 2020/0306086 A1 | 10/2020 | Da Silva Curiel et al. |
| 2020/0345549 A1 | 11/2020 | Lu et al. |
| 2021/0015665 A1 | 1/2021 | Hacker et al. |
| 2021/0030590 A1 | 2/2021 | Blanda et al. |
| 2021/0038158 A1 | 2/2021 | Haffner et al. |
| 2021/0069486 A1 | 3/2021 | Hakim |
| 2021/0106462 A1 | 4/2021 | Sherwood et al. |
| 2021/0137736 A1 | 5/2021 | Cavuto et al. |
| 2021/0161713 A1 | 6/2021 | Bouremel et al. |
| 2021/0196516 A1 | 7/2021 | Ianchulev |
| 2021/0205132 A1 | 7/2021 | Horvath et al. |
| 2021/0212858 A1 | 7/2021 | Tran et al. |
| 2021/0251806 A1 | 8/2021 | Schultz et al. |
| 2021/0282922 A1 | 9/2021 | Cohen-Tzemach et al. |
| 2021/0298948 A1 | 9/2021 | Haffner et al. |
| 2021/0315806 A1 | 10/2021 | Haffner |
| 2021/0330499 A1 | 10/2021 | Wardle et al. |
| 2022/0087865 A1 | 3/2022 | Argento et al. |
| 2022/0142818 A1 | 5/2022 | Chang et al. |
| 2022/0160545 A1 | 5/2022 | Mixter et al. |
| 2022/0160546 A1 | 5/2022 | Mixter et al. |
| 2022/0202613 A1 | 6/2022 | Chang et al. |
| 2022/0339035 A1 | 10/2022 | Lilly et al. |
| 2022/0387216 A1 | 12/2022 | Schultz et al. |
| 2022/0387217 A1 | 12/2022 | Argento et al. |
| 2023/0086856 A1 | 3/2023 | Chang et al. |
| 2023/0092196 A1 | 3/2023 | Argento et al. |

FOREIGN PATENT DOCUMENTS

| | | |
|---|---|---|
| AU | 2018200325 A1 | 2/2018 |
| AU | 2017274654 | 12/2018 |
| AU | 2020201818 | 4/2020 |
| AU | 2017439185 | 5/2020 |
| AU | 20198412569 | 10/2020 |
| BR | 112017025859 A2 | 8/2018 |
| BR | 112020008969 | 10/2020 |
| CA | 2987953 A1 | 12/2016 |
| CA | 3080713 | 5/2019 |
| CA | 3093160 | 9/2019 |
| CN | 104490515 | 4/2015 |
| CN | 106726124 | 5/2017 |
| CN | 108743016 A | 11/2018 |
| CN | 111405875 | 7/2020 |
| CO | 2020011460 | 11/2020 |
| DE | 10217061 | 3/2003 |
| DE | 102010015447 A1 | 10/2011 |
| DE | 102017124885 A1 | 4/2019 |
| DE | 102018112065 A1 | 11/2019 |
| DE | 102019204846 A1 | 10/2020 |
| EP | 1292256 A1 | 3/2003 |
| EP | 1737531 A2 | 1/2007 |
| EP | 3302381 A1 | 4/2018 |
| EP | 1765234 | 10/2019 |
| EP | 2999430 | 11/2019 |

(56) References Cited

FOREIGN PATENT DOCUMENTS

| | | |
|---|---|---|
| EP | 2677981 | 4/2020 |
| EP | 3659495 | 6/2020 |
| EP | 3518846 | 8/2020 |
| EP | 3666236 | 8/2020 |
| EP | 3687374 | 8/2020 |
| EP | 3706653 | 9/2020 |
| EP | 3730104 | 10/2020 |
| EP | 3735947 | 11/2020 |
| EP | 3773377 | 2/2021 |
| EP | 3846747 | 7/2021 |
| EP | 3846748 | 7/2021 |
| EP | 3329884 | 8/2021 |
| EP | 2389138 | 9/2021 |
| EP | 3870120 | 9/2021 |
| EP | 3313335 | 11/2021 |
| ES | 2725550 | 9/2019 |
| HK | 1252748 | 5/2019 |
| HU | E043303 | 8/2019 |
| JP | 5576427 B2 | 8/2014 |
| JP | 2018519892 | 7/2018 |
| JP | 2018130580 | 8/2018 |
| JP | 2019517366 | 6/2019 |
| JP | 2019205934 | 12/2019 |
| JP | 2020049361 | 4/2020 |
| KR | 2018015684 A | 2/2018 |
| KR | 20190019966 | 2/2019 |
| KR | 20200021551 | 2/2020 |
| KR | 20200059305 | 5/2020 |
| PL | 2640455 | 8/2019 |
| PT | 2640455 | 5/2019 |
| RU | 2687764 | 5/2019 |
| RU | 2018142990 | 6/2020 |
| SG | 11202008604 | 10/2020 |
| TR | 201906873 | 6/2019 |
| WO | WO2004081613 | 9/2004 |
| WO | WO2007011302 A1 | 1/2007 |
| WO | WO2010111528 | 9/2010 |
| WO | WO2014130574 | 8/2014 |
| WO | WO2016100500 | 6/2016 |
| WO | WO2016149425 | 9/2016 |
| WO | WO2016196841 A1 | 12/2016 |
| WO | WO2018229766 | 12/2018 |
| WO | WO2019018807 | 1/2019 |
| WO | WO2019094004 A1 | 5/2019 |
| WO | WO2019165053 | 8/2019 |
| WO | WO2019172940 | 9/2019 |
| WO | WO2020150663 | 7/2020 |
| WO | WO2020215068 | 10/2020 |
| WO | WO2020223491 | 11/2020 |
| WO | WO2020231993 | 11/2020 |
| WO | WO2020247365 | 12/2020 |
| WO | WO2020261184 | 12/2020 |
| WO | WO2021007294 | 1/2021 |
| WO | WO2021007296 | 1/2021 |
| WO | WO2021028703 | 2/2021 |
| WO | WO2021068078 | 4/2021 |
| WO | WO2021072315 | 4/2021 |
| WO | WO2021072317 | 4/2021 |
| WO | WO2021113730 | 6/2021 |
| WO | WO2021142255 | 7/2021 |
| WO | WO2021151007 | 7/2021 |
| WO | WO2021163566 | 8/2021 |
| WO | WO2021168130 | 8/2021 |
| WO | WO2021174298 | 9/2021 |
| WO | WO2021176332 | 9/2021 |
| WO | WO2021188952 | 9/2021 |
| WO | WO2021204312 | 10/2021 |
| WO | WO2021212007 | 10/2021 |
| WO | WO2021230887 | 11/2021 |
| WO | WO2022220861 | 10/2022 |
| WO | WO2023004067 | 1/2023 |
| WO | WO2023278452 | 1/2023 |
| WO | WO2023009366 | 2/2023 |
| ZA | 201708295 | 5/2020 |

OTHER PUBLICATIONS

Keulegan et al. "Pressure Losses for Fluid Flow in Curved Pipes," Journal of Research of the National Bureau of Standards, vol. 18, Jan. 31, 1937 (Jan. 31, 1937), 26 pages.
Olsen et al. "Human sclera: thickness and surface area," American Journal of Ophthalmology, vol. 125, issue. 2, https://pubmed.ncbi.nlm.nih.gov/9467451, Feb. 1, 1998 (Feb. 1, 1998), 1 page.
International Search Report and Written Opinion received for PCT Application No. PCT/US22/048863, filed on Nov. 3, 2022, Applicant: Shifamed Holdings, LLC, dated Feb. 16, 2023, 13 pages.
International Search Report and Written Opinion received for PCT Application No. PCT/US18/43158, filed on Jul. 20, 2018, Applicant: Shifamed Holdings, LLC, dated Nov. 23, 2018, 12 pages.
International Search Report and Written Opinion received for PCT Application No. PCT/US20/14186, filed on Jan. 17, 2020, Applicant: Shifamed Holdings, LLC, dated Jun. 4, 2020, 13 pages.
International Search Report and Written Opinion received for PCT Application No. PCT/US21/14774, filed on Jan. 22, 2021, Applicant: Shifamed Holdings, LLC, dated May 12, 2021, 10 pages.
International Search Report and Written Opinion received for PCT Application No. PCT/US21/17962, filed on Feb. 12, 2021, Applicant: Shifamed Holdings, LLC, dated Jun. 7, 2021, 12 pages.
International Search Report and Written Opinion received for PCT Application No. PCT/US21/23238, filed on Mar. 19, 2021, Applicant: Shifamed Holdings, LLC, dated Jul. 8, 2021, 10 pages.
International Search Report and Written Opinion received for PCT Application No. PCT/US21/18601, filed on Feb. 18, 2021, Applicant: Shifamed Holdings, LLC, dated Jul. 19, 2021, 12 pages.
International Search Report and Written Opinion received for PCT Application No. PCT/US21/27742, filed on Apr. 16, 2021, Applicant: Shifamed Holdings, LLC, dated Oct. 7, 2021, 13 pages.
International Search Report and Written Opinion received for PCT Application No. PCT/US21/49140, filed on Sep. 3, 2021, Applicant: Shifamed Holdings, LLC, dated Dec. 7, 2021, 22 pages.
International Search Report and Written Opinion received for PCT Application No. PCT/US21/55258, filed on Oct. 15, 2021, Applicant: Shifamed Holdings, LLC, dated Feb. 28, 2022, 18 pages.
International Search Report and Written Opinion received for PCT Application No. PCT/US20/55144, filed on Oct. 9, 2020, Applicant: Shifamed Holdings, LLC, dated Feb. 1, 2021, 16 pages.
International Search Report and Written Opinion received for PCT Application No. PCT/US20/55141, filed on Oct. 9, 2020, Applicant: Shifamed Holdings, LLC, dated Jan. 29, 2021, 11 pages.
International Search Report and Written Opinion received for PCT Application No. PCT/US22/13336, filed on Jan. 21, 2022, Applicant: Shifamed Holdings, LLC, dated Apr. 11, 2022, 9 pages.
International Search Report and Written Opinion received for PCT Application No. PCT/US22/52002, filed on Dec. 6, 2022, Applicant: Shifamed Holdings, LLC, dated Mar. 21, 2023, 11 pages.

ADJUSTABLE FLOW GLAUCOMA SHUNTS HAVING NON-LINEARLY ARRANGED FLOW CONTROL ELEMENTS, AND ASSOCIATED SYSTEMS AND METHODS

CROSS-REFERENCE TO RELATED APPLICATIONS

This application is a 35 U.S.C. § 371 U.S. National Phase application of International Patent Application No. PCT/US2021/018601, filed Feb. 18, 2021, which claims priority to the following applications:

U.S. Provisional Patent Application No. 62/978,210, filed Feb. 18, 2020; and

U.S. Provisional Patent Application No. 63/018,393, filed Apr. 30, 2020.

The foregoing applications are incorporated herein by reference in their entireties. Further, components and features of embodiments disclosed in the applications incorporated by reference may be combined with various components and features disclosed and claimed in the present application.

TECHNICAL FIELD

The present technology generally relates to implantable medical devices and, in particular, to intraocular systems, devices, and associated methods for selectively controlling fluid flow between different portions of a patient's eye.

BACKGROUND

Glaucoma is a degenerative ocular condition involving damage to the optic nerve that can cause progressive and irreversible vision loss. Glaucoma is frequently associated with ocular hypertension, an increase in pressure within the eye, and may result from an increase in production of aqueous humor ("aqueous") within the eye and/or a decrease in the rate of outflow of aqueous from within the eye into the blood stream. Aqueous is produced in the ciliary body at the boundary of the posterior and anterior chambers of the eye. It flows into the anterior chamber and eventually into the venous vessels of the eye. Glaucoma is typically caused by a failure in mechanisms that transport aqueous out of the eye and into the blood stream.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

The present technology is directed to adjustable shunts for treating glaucoma. In particular, some embodiments provide shunts having a plurality of individually actuatable flow control elements that can control the flow of fluid through associated ports of the shunt. In some embodiments, each flow control element is shaped and sized for movement along a given actuation axis. In some embodiments, at least two flow control elements of a plurality of flow control elements are disposed to have different (e.g., non-parallel) actuation axes. The non-linear arrangement of the plurality of flow control elements may advantageously reduce an (e.g., average) distance of the flow control elements from a collection and/or drainage region of the adjustable shunt. The non-linear arrangement of the plurality of flow control elements may also advantageously reduce a linear extent (e.g., length) of an adjustable shunt for a given number of flow control elements (e.g., reduced with respect to a linear arrangement of flow control elements).

Each individually actuatable flow control element can be actuated to modify a flow resistance of a corresponding port, thereby impeding or facilitating flow through the port. At times, modifying a flow resistance through the shunt may include blocking and/or unblocking a flow port. It will be appreciated that, with respect to the flow control structures and fluid flow rates of the present disclosure, "blocking" and/or "unblocking" may be non-binary first and second states. For example, blocking a flow port may refer to partially closing the flow port and unblocking the flow port may refer to partially opening the flow port. The first and second states may comprise flow rates that are significantly different with respect to one another. In some embodiments a blocked flow port may permit at least some fluid flow therethrough (e.g., have non-zero flow). For example, in some embodiments an unblocked flow port may be less than fully open and facilitate an intermediate flow that is less than a maximal flow rate. Adjustment to the shunt may include modification in terms of measured flow, for example a volume (e.g., microliters) of aqueous flow. Adjustment to the shunt may include modification in terms of clinical effect, for example, reduction in intraocular pressure (IOP). Accordingly, the shunts described herein can be manipulated into a variety of configurations that provide different drainage rates based on the combination of ports that are blocked or unblocked. The various combinations of blocked and unblocked ports provide a titratable glaucoma therapy for draining aqueous from the anterior chamber of the eye. In some embodiments, the flow control elements can be non-invasively adjusted after the shunt is implanted in the eye to allow for post-implant adjustments.

In some embodiments, the present technology includes a flow control assembly for modifying flow in an adjustable intraocular shunt. The flow control assembly can include a plurality of locking mechanisms, a plurality of anchoring elements coupled with the locking mechanisms, and a plurality of non-linearly arranged flow control elements coupled with the plurality of anchoring elements. In some embodiments, each flow control element includes a first actuation element, a second actuation element, and a gating element disposed therebetween. In some embodiments, a portion of a first flow control element is coupled with a portion of a second flow control element. For example, an end of a first flow control element is coupled with a beginning of a second flow control element.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but that are not described in detail with respect to FIGS. 1A-7.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%. Reference throughout this specification to the term "resistance" refers to fluid resistance unless the context clearly dictates otherwise. The terms "drainage rate," "flow rate," and "flow" are used interchangeably to describe the movement of fluid through a structure.

Although certain embodiments herein are described in terms of shunting fluid from an anterior chamber of an eye, one of skill in the art will appreciate that the present technology can be readily adapted to shunt fluid from and/or between other portions of the eye, or, more generally, from and/or between a first body region and a second body region. Moreover, while the certain embodiments herein are described in the context of glaucoma treatment, any of the embodiments herein, including those referred to as "glaucoma shunts" or "glaucoma devices" may nevertheless be used and/or modified to treat other diseases or conditions, including other diseases or conditions of the eye or other body regions. For example, the systems described herein can be used to treat diseases characterized by increased pressure and/or fluid build-up, including but not limited to heart failure (e.g., heart failure with preserved ejection fraction, heart failure with reduced ejection fraction, etc.), pulmonary failure, renal failure, hydrocephalus, and the like. Moreover, while generally described in terms of shunting aqueous, the systems described herein may be applied equally to shunting other fluid, such as blood or cerebrospinal fluid, between the first body region and the second body region.

The headings provided herein are for convenience only and do not interpret the scope or meaning of the claimed present technology.

A. Intraocular Shunts for Glaucoma Treatment

Glaucoma refers to a group of eye diseases associated with damage to the optic nerve which eventually results in vision loss and blindness. As noted above, glaucoma is a degenerative ocular condition characterized by an increase in pressure within the eye resulting from an increase in production of aqueous within the eye and/or a decrease in the rate of outflow of aqueous from within the eye into the blood stream. The increased pressure leads to injury of the optic nerve over time. Unfortunately, patients often do not present with symptoms of increased intraocular pressure until the onset of glaucoma. As such, patients typically must be closely monitored once increased pressure is identified even if they are not symptomatic. The monitoring continues over the course of the disease so clinicians can intervene early to stem progression of the disease. Monitoring pressure requires patients to visit a clinic site on a regular basis which is expensive, time-consuming, and inconvenient. The early stages of glaucoma are typically treated with drugs (e.g., eye drops) and/or laser therapy. When drug/laser treatments no longer suffice, however, surgical approaches can be used. Surgical or minimally invasive approaches primarily attempt to increase the outflow of aqueous from the anterior chamber to the blood stream either by the creation of alternative fluid paths or the augmentation of the natural paths for aqueous outflow.

Figure 1A:
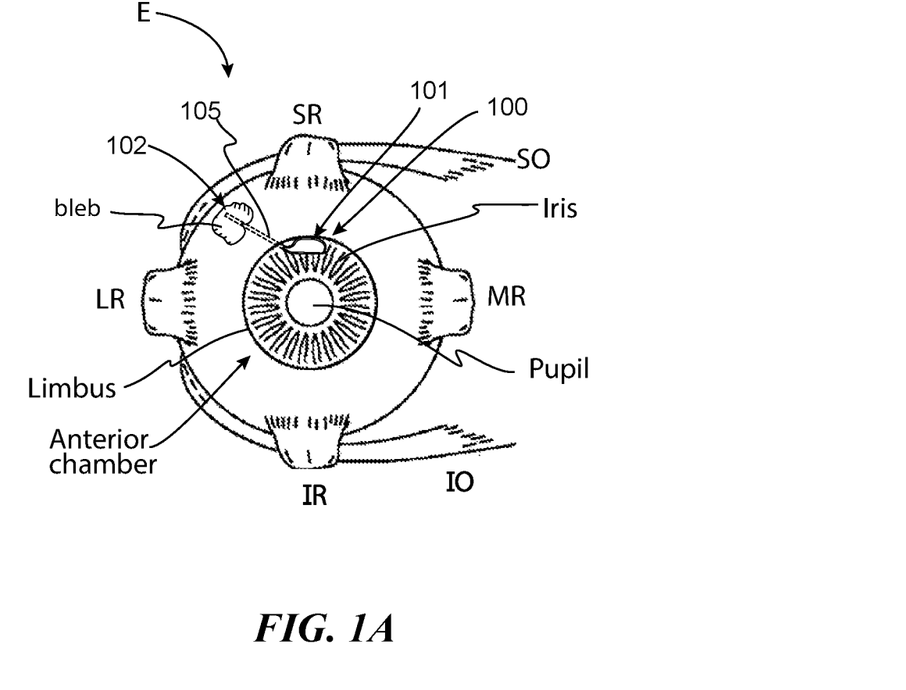
FIG. 1A is a simplified front view of an eye with an implanted shunt configured in accordance with an embodiment of the present technology.
Figure 1B:
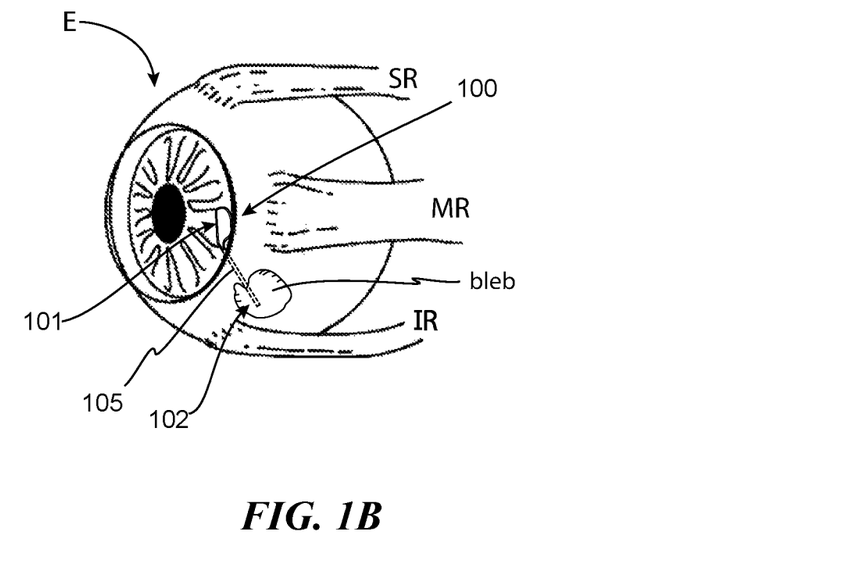
FIG. 1B is an isometric view of an eye and implanted shunt configured in accordance with an embodiment of the present technology.

FIGS. 1A and 1B illustrate a human eye E and suitable location(s) in which a shunt may be implanted within the eye E in accordance with embodiments of the present technology. More specifically, FIG. 1A is a simplified front view of the eye E with an implanted shunt 100, and FIG. 1B is an isometric view of the eye E and the shunt 100 of FIG. 1A. Referring first to FIG. 1A, the eye E includes a number of muscles to control its movement, including a superior rectus SR, inferior rectus IR, lateral rectus LR, medial rectus MR, superior oblique SO, and inferior oblique IO. The eye E also includes an iris, pupil, and limbus.

Referring to FIGS. 1A and 1B together, the shunt 100 can have a drainage element 105 (e.g., a drainage tube) positioned such that an inflow portion 101 is positioned in an anterior chamber of the eye E, and an outflow portion 102 is positioned at a different location within the eye E, such as a bleb space. The shunt 100 can be implanted in a variety of orientations. For example, when implanted, the drainage element 105 may extend in a superior, inferior, medial, and/or lateral direction from the anterior chamber. Depending upon the design of the shunt 100, the outflow portion 102 can be placed in a number of different suitable outflow locations (e.g., between the choroid and the sclera, between the conjunctiva and the sclera, etc.).

Outflow resistance can change over time for a variety of reasons, e.g., as the outflow location goes through its healing process after surgical implantation of a shunt (e.g., shunt 100) or further blockage in the drainage network from the anterior chamber through the trabecular meshwork, Schlemm's canal, the collector channels, and eventually into the vein and the body's circulatory system. Accordingly, a clinician may desire to modify the shunt after implantation to either increase or decrease the outflow resistance in response to such changes or for other clinical reasons. For example, in many procedures the shunt is modified at implantation to temporarily increase its outflow resistance. After a period of time deemed sufficient to allow for healing of the tissues and stabilization of the outflow resistance, the modification to the shunt is reversed, thereby decreasing the outflow resistance. In another example, the clinician may implant the shunt and after subsequent monitoring of intraocular pressure determine a modification of the drainage rate through the shunt is desired. Such modifications can be invasive, time-consuming, and/or expensive for patients. If such a procedure is not followed, however, there is a high likelihood of creating hypotony (excessively low eye pressure), which can result in further complications, including damage to the optic nerve. In contrast, intraocular shunting systems configured in accordance with embodiments of the present technology allow the clinician to selectively adjust the flow of fluid through the shunt after implantation without additional invasive surgical procedures.

The shunts described herein can be implanted having a first drainage rate and subsequently remotely adjusted to achieve a second, different drainage rate. The adjustment can be based on the needs of the individual patient. For example, the shunt may be implanted at a first lower flow rate and subsequently adjusted to a second higher flow rate as clinically necessary. The shunts described herein can be delivered using either ab interno or ab externo implant techniques, and can be delivered via needles. The needles can have a variety of shapes and configurations to accommodate the various shapes of the shunts described herein. Details of the implant procedure, the implant devices, and bleb formation are described in greater detail in International Patent Application No. PCT/US20/41152, filed Jul. 8, 2020, the disclosure of which is incorporated by reference herein for all purposes.

In many of the embodiments described herein, the flow control assemblies are configured to introduce features that selectively impede or attenuate fluid flow through the shunt during operation. In this way, the flow control assemblies can incrementally or continuously change the flow resistance through the shunt to selectively regulate pressure and/or flow. The flow control assemblies configured in accordance with the present technology can accordingly adjust the level of interference or compression between a number of different positions, and accommodate a multitude of variables (e.g., IOP, aqueous production rate, native aqueous outflow resistance, and/or native aqueous outflow rate) to precisely regulate flow rate through the shunt.

The disclosed flow control assemblies can be operated using energy. This feature allows such devices to be implanted in the patient and then modified/adjusted over time without further invasive surgeries or procedures for the patient. Further, because the devices disclosed herein may be actuated via energy from an external energy source (e.g., a laser), such devices do not require any additional power to maintain a desired orientation or position. Rather, the actuators/fluid resistors disclosed herein can maintain a desired position/orientation without power. This can significantly increase the usable lifetime of such devices and enable such devices to be effective long after the initial implantation procedure.

B. Operation of Actuation Elements

Some embodiments of the present technology include actuation assemblies (e.g., flow control assemblies or flow control mechanisms) that have at least two actuation elements coupled to a moveable element (e.g., a gating element). As described in detail below, the moveable element can be formed to interface with (e.g., at least partially block) a corresponding port. The port can be an inflow port or an outflow port. Movement of the actuation elements generates movement of the moveable element. The movement can be translational and/or rotational.

The actuation element(s) can include a shape memory material (e.g., a shape memory alloy, or a shape memory polymer). Movement of the actuation element(s) can be generated through applied stress and/or use of a shape memory effect (e.g., as driven by a change in temperature). The shape memory effect enables deformations that have altered an element from its preferred geometric configuration (e.g., original or fabricated configuration, shape-set configuration, heat-set configuration, etc.) to be largely or entirely reversed during operation of the flow control assembly. For example, thermal actuation (heating) can reverse deformation(s) by inducing a change in state (e.g., phase change) in the actuator material, inducing a temporary elevated internal stress that promotes a shape change toward the preferred geometric configuration. For a shape memory alloy, the change in state can be from a martensitic phase (alternatively, R-phase) to an austenitic phase. For a shape memory polymer, the change in state can be via a glass transition temperature or a melting temperature. The change in state can reverse deformation(s) of the material—for example, deformation with respect to its preferred geometric configuration—without any (e.g., externally) applied stress to the actuation element. That is, a deformation that is present in the material at a first temperature (e.g., body temperature) can be (e.g., thermally) recovered and/or altered by raising the material to a second (e.g., higher) temperature. Upon cooling (and changing state, e.g., back to martensitic phase), the actuation element retains its preferred geometric configuration. With the material in this relatively cooler-temperature condition it may require a lower force or stress to thermoelastically deform the material, and any subsequently applied external stress can cause the actuation element to once again deform away from the original geometric configuration.

The actuation element(s) can be processed such that a transition temperature at which the change in state occurs (e.g., the austenite start temperature, the austenite final temperature, etc.) is above a threshold temperature (e.g., body temperature). For example, the transition temperature can be set to be about 45 deg. C., about 50 deg. C., about 55 deg. C., or about 60 deg. C. In some embodiments, the actuator material is heated from body temperature to a temperature above the austenite start temperature (or alternatively above the R-phase start temperature) such that an upper plateau stress (e.g., "UPS_body temperature") of the material in a first state (e.g., thermoelastic martensitic phase, or thermoelastic R-phase at body temperature) is lower than an upper plateau stress (e.g., "UPS_actuated temperature") of the material in a heated state (e.g., superelastic state), which achieves partial or full free recovery. For example, the actuator material can be heated such that UPS_actuated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase at body temperature") is lower than a lower plateau stress (e.g., "LPS") of the material in a heated state (e.g., superelastic state), which achieves partial or full free recovery. For example, the actuator material can be aged such that LPS_activated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase) is higher than a lower plateau stress of the material in a heated state, which achieves partial free recovery. For example, the actuator material can be aged such that LPS_activated temperature<UPS_body temperature.

The flow control assembly can be formed such that the actuation elements have substantially the same preferred geometric configuration (e.g., memory shape, or length, L0).

The flow control assembly can be assembled such that, upon introduction into a patient (e.g., implantation), at least one (e.g., a first) actuation element/shape memory element has been deformed with respect to its preferred geometric configuration (e.g., to have $L1 \neq L0$), while at least one other opposing (e.g., a second) actuation element/shape memory element positioned adjacent to the first actuation element is substantially at its preferred geometric configuration (e.g., L0). In other embodiments, however, both the first and second actuation elements may be deformed with respect to their corresponding preferred geometric configuration upon introduction into the patient (e.g., the first actuation element is contracted relative to its preferred geometric configuration and the second actuation element is expanded relative to its preferred geometric configuration).

In some embodiments of the present technology, $L1>L0$—for example, the deformed first actuation element is elongated with respect to its preferred "shape memory" length. In some embodiments, $L1<L0$—for example, the deformed first actuation element is compressed with respect to its preferred shape memory length. The flow control assembly can be formed such that, in operation, its overall dimension (e.g., overall length) is substantially fixed (e.g., $L0+L1=$ a constant). For example, (e.g., outermost) ends of the actuation elements can be fixed, such that movement of the actuation elements occurs between the points of fixation. The overall geometry of the actuation elements, along with the lengths, can be selected such that, in operation, deformation within the actuation elements remains below about 10%, about 9%, about 8%, about 7%, or about 6%.

The (e.g., first and second) actuation elements are arranged such that a movement (e.g., deflection or deformation) of the first actuation element/first shape memory element is accompanied by (e.g., causes) an opposing movement of the second actuation element/second shape memory element. The movement can be a deflection or a deformation. In operation, selective heating of the first actuation element of the flow control assembly causes it to move to and/or toward its preferred geometric configuration (e.g., revert from L1 to L0), moving the coupled moveable element. At the same time, the elongation of the first actuation element is accompanied by (e.g., causes) a compression of the second actuation element (e.g., from L0 to L1). The second actuation element is not heated (e.g., remains at body temperature), and therefore the second actuation element deforms (e.g., remains martensitic and compresses). The first actuation element cools following heating, and returns to a state in which it can be plastically deformed. To reverse the configuration of the flow control assembly (e.g., the position of the moveable element), the second actuation element is heated to move to and/or toward its preferred geometric configuration (e.g., from L1 to L0). The return of the second actuation element to its preferred geometric configuration causes the moveable element to move back to its prior position, and compresses the first actuation element (e.g., from L0 to L1). The position of the moveable element for the flow control assembly can be repeatably toggled (e.g., between open and closed) by repeating the foregoing operations. The heating of an actuation element can be accomplished via application of incident energy (e.g., via a laser or inductive coupling). Further, as mentioned above, the source of the incident energy may be external to the patient (e.g., non-invasive).

C. Flow Control Assemblies for Intraocular Shunting Systems

Figure 2:
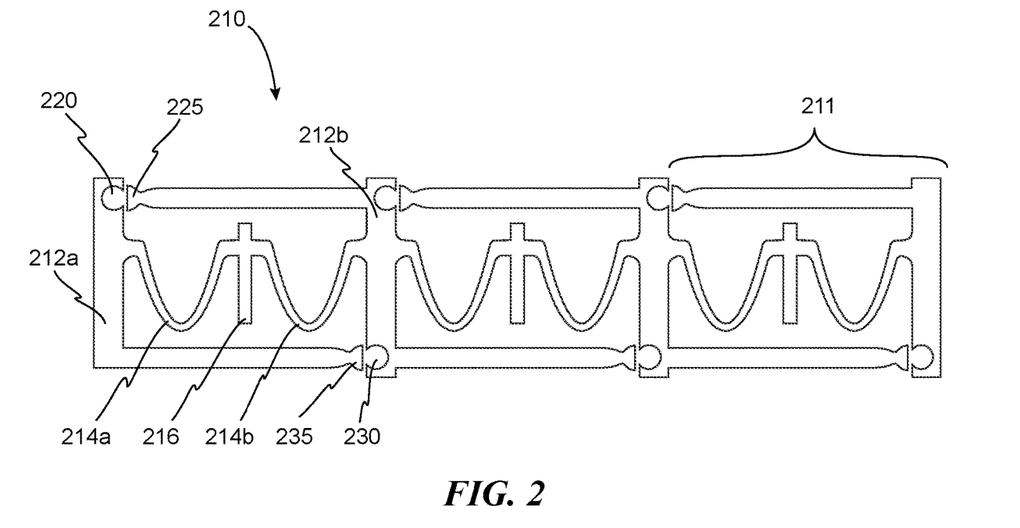
FIG. 2 illustrates a flow control assembly in accordance with an embodiment of the present technology.

FIG. 2 illustrates a flow control assembly 210 for controlling the flow of fluid through a shunt and configured in accordance with embodiments of the present technology. In the illustrated embodiment, the flow control assembly 210 includes a plurality of linearly arranged flow control elements 211. When the flow control assembly 210 is coupled to a shunt or other drainage element (not shown in FIG. 2), each individual flow control element 211 can interface with and/or otherwise be configured to control the flow of fluid through corresponding ports (e.g., inflow ports, outflow ports, etc.) on the shunt. Each flow control element 211 can be individually actuatable, such that any combination of inflow or outflow ports (not shown) can be blocked or unblocked to adjust flow through the adjustable shunt. Each flow control element 211 includes a pair of anchors 212 (e.g., a first anchor 212a and second anchor 212b) spaced apart along a length of the flow control assembly 210. Each flow control element 211 further includes a pair of actuation elements 214 (e.g., a first actuation element 214a and a second actuation element 214b) and a gating element 216 that is positioned generally between each pair of actuation elements. The gating element 216 is dimensioned and positioned such that, upon actuation of an actuation element, it is moved to selectively block (or at least partially block) and unblock (or at least partially unblock) an inflow or outflow port on the shunt.

The gating element 216 can be moved by actuating the actuation elements 214. For example, actuating the first actuation element 214a can move the gating element 216 in a first direction, and actuating the second actuation element 214b can move the gating element 216 in a second direction generally opposite the first direction. To facilitate the foregoing movement of the gating element 216, the actuation elements 214 can be composed at least partially of a shape memory material (e.g., a shape memory alloy) or other suitable material that is configured to change shape upon application of energy. For example, in some embodiments the actuation elements 214 are composed of nitinol. In such embodiments, the actuation elements 214 (and/or regions thereof) can be transitionable at least between a first material phase or state (e.g., a martensitic state, a R-phase, a composite state between martensitic and R-phase, etc.) and a second material phase or state (e.g., an austenitic state, an R-phase state, a composite state between austenitic and R-phase, etc.). In the first material state, the actuation element or select region thereof may be deformable (e.g., plastic, malleable, compressible, expandable, etc.). In the second material state, the actuation element or select region thereof may have a preference toward a specific preferred geometry (e.g., original geometry, manufactured or fabricated geometry, heat set geometry, etc.). As described below, the actuation elements 214 can be individually and/or selectively transitioned between the first material state and the second material state by applying energy (e.g., heat, light, etc.) to the actuation element to heat the actuation element above a transition temperature (e.g., a phase transition temperature). If the actuation element is deformed relative to its preferred geometry, the transition from the first material state to the second material state can induce a dimensional change in the actuation element. In some embodiments, the dimensional change is an expansion. In some embodiments, the dimensional change is a contraction (e.g., compression). In some embodiments, the energy is applied from an energy source positioned external to the patient (e.g., a laser), which can enable a user to non-invasively adjust a position of the gating element 216.

The flow control element 211 or a portion thereof (e.g., the first actuation element 214a or the second actuation element 214b) can be actuated to move (e.g., translate) the gating element 216 relative to the drainage element (not shown) between the first anchor 212a and the second anchor 212b. This movement of the gating element 216 can cause it to block (e.g., partially or fully block) and/or unblock (e.g., partially or fully unblock) the associated port (not shown) on the drainage element. For example, in embodiments in which the first actuation element 214a is compressed relative to its preferred geometry, heating the first actuation element 214a above its transition temperature can cause the first actuation element 214a to expand and/or stiffen (thereby expanding in length). Because the first anchor 212a and the second anchor 212b are secured in place (e.g., they do not move relative to the drainage element), the first actuation element 214a pushes the gating element 216 away from the first anchor 212a as it expands (and toward the second anchor 212b). Likewise, heating the second actuation element 214b causes the second actuation element 214b to expand, which pushes the gating element 216 away from the second anchor 212b and back towards the first anchor 212a. Additional details regarding the operation of shape memory actuators for glaucoma shunts are described in U.S. Patent App. Publication No. 2020/0229982 and International Patent Application Nos. PCT/US20/55144, PCT/US20/55141, and PCT/US21/14774, the disclosures of which are incorporated by reference herein in their entireties and for all purposes.

Each flow control element 211 further includes a locking element. In an unlocked configuration, the components of the locking elements are spaced apart and the actuation elements of a flow control element are substantially unstrained. In a locked configuration, the components of the locking elements are coupled, thereby imparting strain upon the actuation elements that are positioned between the anchor elements. In the example of FIG. 2, a locking element includes a retention feature (e.g., an aperture 220) and an engagement feature (e.g., tab 225). The flow control element 211 can be transitioned from the unlocked configuration to the locked configuration by securing (e.g., releasably securing) the engagement feature to the retention feature. In some embodiments, a flow control element includes at least two locking elements, for example, second aperture 230 and second tab 235 as shown in example FIG. 2. The anchors of the flow control assembly can be secured to the adjustable shunt such that they do not move when the actuation elements are actuated. For example, the anchors may be secured thereto via a bonding, a friction fit, an interference fit, or other suitable attachment mechanism.

Figure 3:
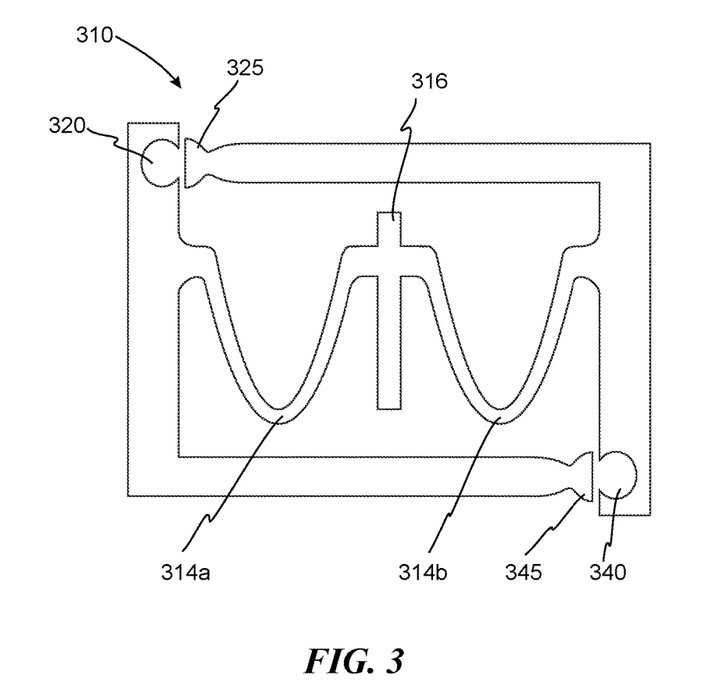
FIG. 3 illustrates a flow control assembly in accordance with an embodiment of the present technology.

FIG. 3 depicts an example of a single flow control element 310, which can be similar to or the same as the flow control element 211 described with reference to FIG. 2. For example, the flow control element 310 can include a first actuation element 314a, a second actuation element 314b (collectively referred to as the actuation elements 314), and a gating element. The flow control element 310 can further include a first locking retention feature (e.g., aperture 320) and a first locking engagement feature (e.g., tab 325), and a second locking retention feature (e.g., aperture 340) and a second locking engagement feature (e.g., tab 345).

The actuation elements 314, which can be composed at least partially of a shape memory material and operate in a manner generally similar to that described with respect to the actuation elements 214 of FIG. 2, can each have a curved and/or bent shape with at least one peak (e.g., an apex, a bend region, etc.). In some embodiments, the geometry of the actuation elements 314 is configured such that any deformation and/or strain is concentrated mostly or entirely at or near the peak region. When loaded (e.g., locked) and/or deformed (e.g., relative to their preferred geometric configurations), the strain (e.g., maximum strain) at or near the peak region can be about 4.5% or less. Although FIG. 3 illustrate the peaks of the actuation elements 314 as being oriented vertically downward, in other embodiments the peaks of the actuation elements 314 can be oriented vertically upward. Optionally, the peak of one actuation element can be oriented vertically downward while the peak of the other actuation element can be oriented vertically upward. In some embodiments, the actuation elements 314 are actuatable (e.g., via a shape memory effect) between a first configuration and a second configuration, the second configuration having a different geometry (e.g., size and/or shape) than the first configuration.

In some embodiments, a flow control assembly is formed to have a least two flow control elements arranged in a non-coaxial manner, rather than the linear arrangement shown in FIG. 2. A non-coaxial (e.g., non-linear) arrangement of flow control elements can enable a relatively close spacing between actuation elements of differing flow control elements (close with respect to a given locus). For example, the flow control elements can be arranged around a central region of the flow control assembly. The region can be a region of a bladder (e.g., portion). The bladder can be a bladder such as is described in International Patent Application Nos. PCT/US20/55144 and PCT/US20/55141previously incorporated by reference herein.

Figure 4:
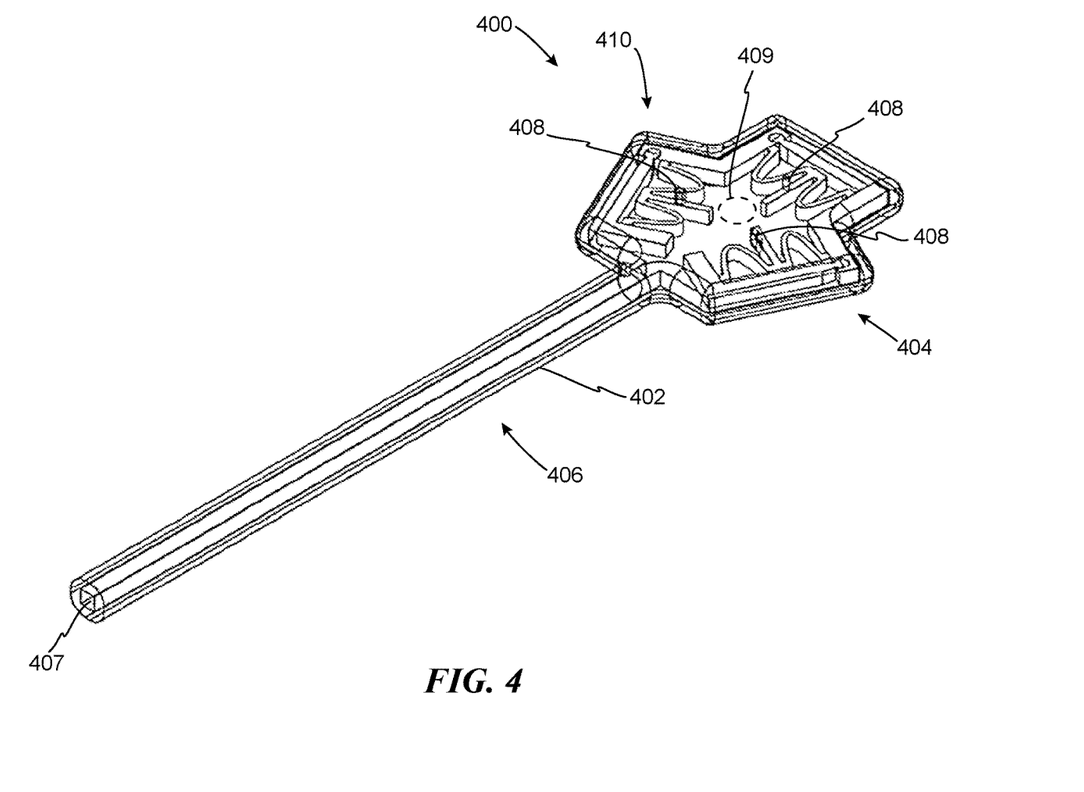
FIG. 4 is an isometric view of an adjustable shunt in accordance with an embodiment of the present technology.

FIG. 4 illustrates an adjustable shunt 400 ("shunt 400") configured in accordance with embodiments of the present technology. Referring first to FIG. 4, the shunt 400 includes a drainage element 402 having a first end portion 404 and a second end portion 406 opposite the first end portion 404. The drainage element can include a drainable tube. The drainage element 402 can have a plurality of first ports 408 (e.g., apertures, perforations, etc.) at or adjacent to the first end portion 404 and a second port 407 at or adjacent the second end portion 406. The plurality of first ports 408 can be arranged about a locus. The locus can be located in a collection region (e.g., collection region 409) of the adjustable shunt. A lumen can extend through the element 402 to fluidly connect the plurality of first ports 408 and the second port 407. In some embodiments, the element 402 can be relatively flat such that its height is less than its width (e.g., the drainage element 402 has an oval, rectangular, or "D-shaped" cross sectional shape). In such embodiments, the drainage element 402 may have an outer diameter (e.g., height) of about 1000 microns (μm) or less, about 400 μm or less, or about 300 μm or less. The drainage element can have an outer diameter value that is between any of the aforementioned values of outer diameter. In some embodiments, the drainage element may have an inner diameter of about 800 μm or less, about 300 μm or less, or about 200 μm or less. The drainage element 402 can have an inner diameter value that is between any of the aforementioned values of inner diameter. In some embodiments, the drainage element 402 can have a length that is about 5 mm, about 6 mm, about 7 mm, about 8 mm, about 9 mm, about 10 mm, or about 15 mm. The drainage element can have a length that is between any of the aforementioned values of length. In other embodiments, the drainage element 402 can be substantially cylindrical. Without wishing to be bound by theory, having a relatively flat profile is expected to advantageously reduce interference with native tissue while providing increased stability of the shunt 400.

The shunt 400 can include a flow control mechanism 410 positioned at the first end portion 404 of the drainage element 402. When the shunt 400 is implanted in an eye, the first end portion 404 can reside within an anterior chamber and the second end portion 406 can reside in a desired outflow location (e.g., a bleb space). In such embodiments, the flow control mechanism 410 is located within the anterior chamber. In other embodiments, the first end portion 404 can reside within the desired outflow location and the second end portion 406 can reside within the anterior chamber. In such embodiments, the flow control mechanism 410 is positioned outside of the anterior chamber (e.g., in the bleb space). Regardless of the orientation of the shunt 400, the shunt 400 is configured to drain aqueous from the anterior chamber when the shunt 400 is implanted in the eye. The shunt 400 may optionally have additional features that help secure the shunt 400 in place when implanted in the eye. For example, the shunt 400 can include arms, anchors, plates, or other suitable features that can secure the shunt 400 to native tissue.

Figure 5:
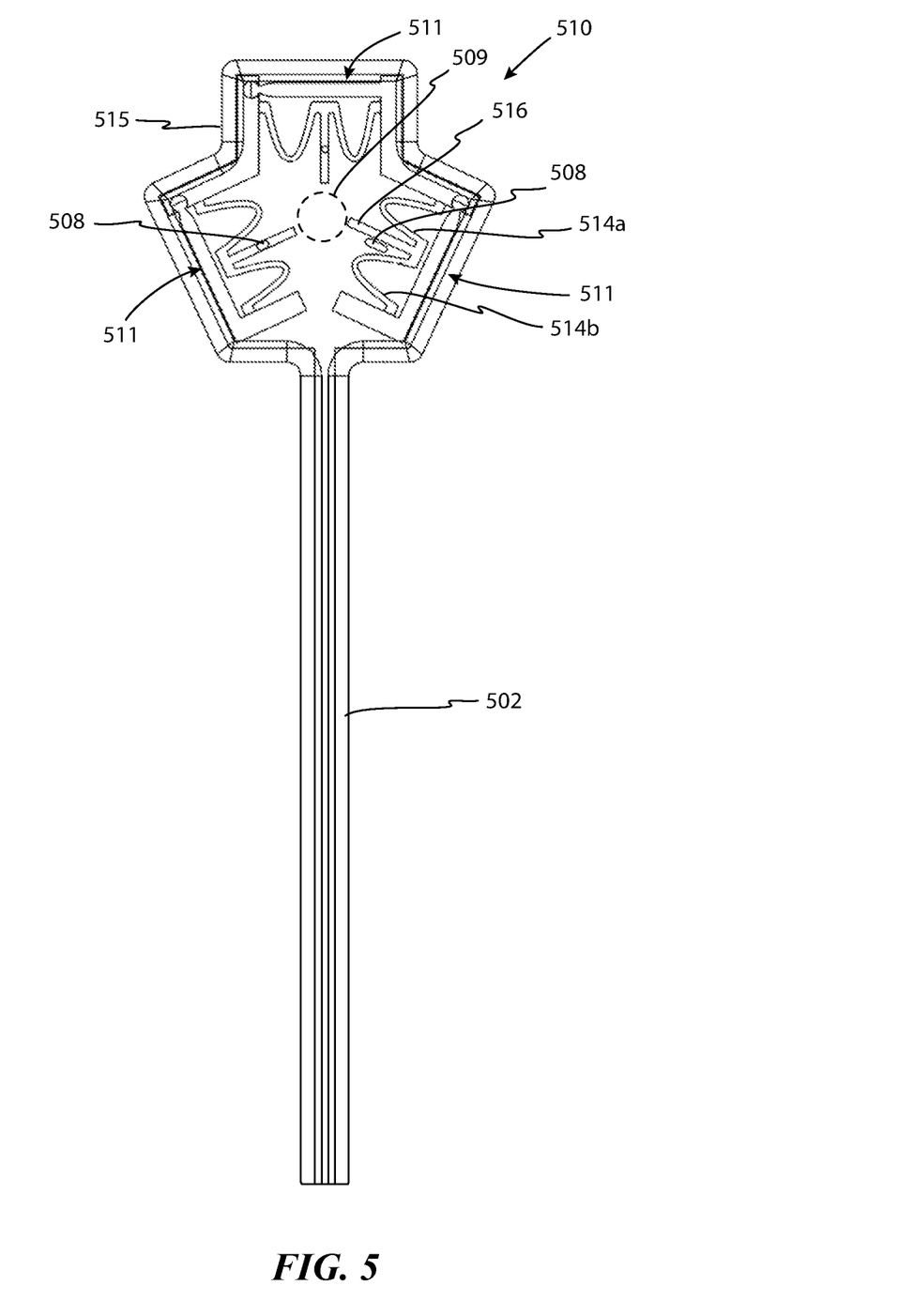
FIG. 5 is a plan view of an adjustable shunt in accordance with an embodiment of the present technology.

Referring now to FIG. 5, a plan view is illustrated of an adjustable shunt 500 ("shunt 500") configured in accordance with embodiments of the present disclosure. The shunt 500 can be similar to or the same as the shunt 400 described above with reference to FIG. 4. For example, the shunt 500 can include a flow control assembly 510 formed and positioned within the shunt 500 to selectively block/unblock a plurality of ports 508. In the example depicted the shunt 500 includes an outer membrane 515 defining the plurality of flow ports 508. The flow control assembly 510 is placed within the outer membrane 515. The outer membrane 515 can be formed of a material suitable for implantation in a human eye. The outer membrane 515 and/or a bladder material can comprise silicone, urethane, hydrogels, poly methyl methacrylate (PMMA), low glass transition ($T_g$) acrylics (e.g., having a $T_g$ of about 50 Celsius or below), polyether ether ketone (PEEK), or polycarbonate. The outer membrane 515 can have a bladder portion that encloses the flow control assembly 510. The bladder portion can have a plurality of holes, slots, or channels that allow aqueous to transit therethrough. The outer membrane 515 can protect the flow control assembly 510 and permit the flow control assembly to move freely without interference from tissue. In some embodiments, the outer membrane 515 can assist in maintaining a drainage bleb open by minimizing tissue ingrowth. In some embodiments, the outer membrane 515 can be shaped and sized to anchor a shunt in a target position when the shunt 500 is implanted in an eye.

The flow control assembly 510 includes a plurality of flow control elements 511. Each of the depicted flow control elements 511 includes a first actuation element (e.g., 514a), a second actuation element (e.g., 514b) (collectively referred to as the actuation elements 514), and a gating element (e.g., 516) that is coupled with and positioned between the first and second actuation elements. The plurality of flow control elements 511 are arranged such that, in operation, actuation thereof enables selective blocking/unblocking of adjacent flow port(s) 508. For example, the actuation elements (e.g., the first actuation element 514a and the second actuation element 514b) can be composed at least in part of a shape memory material such as nitinol, and can be actuated in a manner generally similar to that described for the flow control elements 211 of the shunt 200.

The flow ports 508 (and adjacent flow control elements) are arranged about a (e.g., centralized) collection region 509. The collection region 509 is disposed so as to fluidly couple the inlet and outlet regions of the drainage element 502. The shunt 500 can be manipulated into any number of configurations with all, some, or none of the ports 508 blocked by the gating elements 516. The greater the number of ports 508 that are unblocked, the greater the flow of fluid that is able to drain through the shunt 500. The ports 508 can have the same or different dimensions. In some embodiments, at least two flow ports 508 are positioned at different distances from the collection region 509. In some embodiments, at least two flow ports 508 are positioned at substantially the same distance from the collection region 509. In some embodiments, a distance from a flow port 508 to the collection region 509 is about 200 μm or less, about 400 μm or less, about 600 μm or less, about 800 μm or less, about 1000 μm or less, about 1500 μm or less, or about 2000 μm or less. Each of the ports 508 can be associated with a particular resistance, fluid flow, and/or drainage rate relative to other ports 508. For example, the ports 508 can have relative resistances, fluid flow, and/or drainage rates as described in International Patent Application No. PCT/US21/14774, previously incorporated by reference herein. While FIG. 5 depicts three ports 508, it will be appreciated that a greater or lesser number of ports 508 (and/or corresponding flow control elements 511) may be provided for the shunt 500.

In some embodiments, the actuation elements 514 are configured to retain their shape following application of energy. For example, when energy is applied to the second actuation element 514b to transition a first flow control element from a closed configuration (not shown) to the open configuration shown in FIG. 5, the flow control element 511 can retain the open configuration as shown in FIG. 5 until further energy is applied. Accordingly, once the first flow control element is actuated to unblock the corresponding port 508, the corresponding port 508 remains unblocked until further energy is applied to the first flow control element (e.g., by application of energy to 514a). In other embodiments, the actuation elements may exhibit a (e.g., partial) recoil effect, in which the energized actuation element recoils towards an original shape once the application of energy is terminated.

Figure 6:
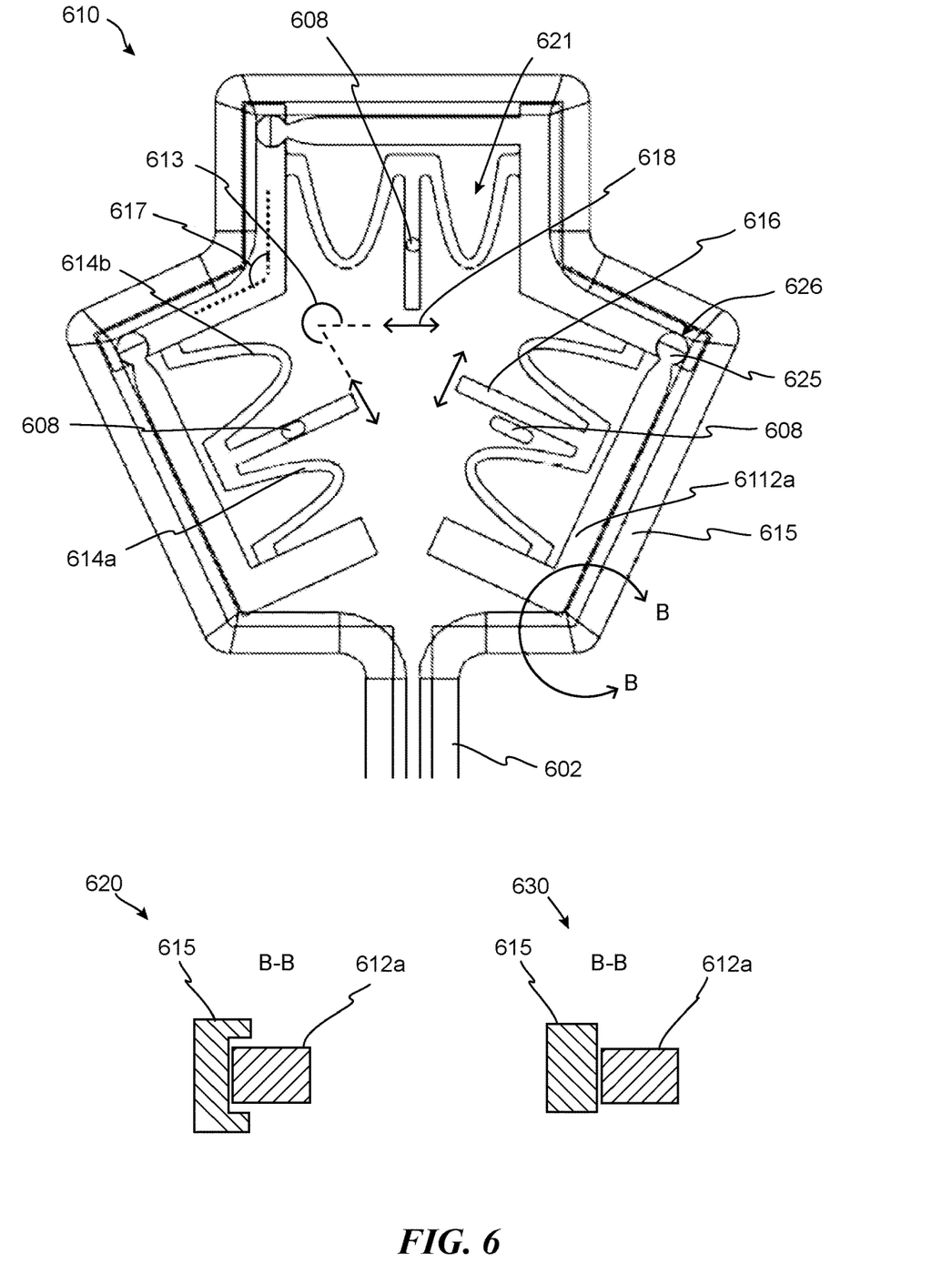
FIG. 6 illustrates a portion of an adjustable shunt in accordance with an embodiment of the present technology.

Referring now to FIG. 6, a portion of an adjustable shunt 600 ("shunt 600") configured in accordance with an embodiment of the present technology is depicted. The shunt 600 can be similar to or the same as the shunts 400 and 500 described above with reference to FIGS. 4 and 5, respectively. For example, the shunt 600 can include a flow control assembly 610 formed and positioned within the shunt 600 to selectively block/unblock a plurality of ports 608. For example, the flow control assembly 610 can have one or more flow control elements 611, with each flow control element 611 including a first actuation element 614a, a second actuation element 614b, and a gating element 616. The actuation elements (e.g., the first actuation element 614a and the second actuation element 614b) can be composed at least in part of a shape memory material such as nitinol, and can be actuated in a manner generally similar to that described for the flow control elements 211 of the shunt 200. The gating element 616 can be configured to interface with (e.g., block, at least partially block, etc.) a corresponding port 608 to control the flow of fluid therethrough, as previously described herein.

The flow control assembly 610 can further include one or more locking elements having an engagement feature 625 and a retention feature 626, such as described with reference to the flow control elements 211 and 310 of FIGS. 2 and 3. The flow control assembly 610 can be formed such that, prior to installation into an outer membrane 615 of the shunt 600 (described below), the locking elements are in an unlocked configuration (i.e., the engagement feature 625 does not engage the retention feature 626, as shown in FIGS. 2 and 3 with reference to the flow control elements 211 and 310). According to embodiments of the present disclosure, in an unlocked configuration, the actuation elements 614 that are connected to the locking elements are in an un-biased (e.g., non-deformed) state. Upon installation of the flow control assembly 610 into the outer membrane 615, the locking elements are secured to form a locked configuration (e.g., the engagement features 625 are placed within the retention features 626). In the locked configuration, the actuation elements that are connected to the locking elements are stressed to impart a strain into a biased state. In the biased state, at least one of the actuation elements (e.g., 614a) is strained to have a configuration (e.g., length) that is other than its preferred geometric configuration (e.g., strained to "L," where $L \neq L_0$). In the biased state, an opposing actuation element (e.g., 614b) can be at its preferred geometric configuration or may also be biased toward a configuration that is different than its preferred geometric configuration.

In some embodiments, the flow control assembly 610 is inserted into a cavity or chamber 621 (e.g., pre-formed cavity or chamber) within/defined by the outer membrane 615. The outer membrane 615 may comprise one or more ports 608 for permitting the passage of fluid from the anterior chamber and into the cavity or chamber. A drainage element or tube 602 that is fluidly coupled with the chamber enables drainage therefrom. In some embodiments, the ports 608 are round and/or oblong in shape. Use of the flow control assembly 610 enables flow control by blocking (or unblocking) any selected number of port(s) 608. An increase in a number of ports 608 that are blocked generates a condition in which less fluid is able to drain from the anterior chamber to the exterior (e.g., to a bleb). In some embodiments, the outer membrane is formed to surround (e.g., encompass) the flow control assembly 610. One or more anchor elements (e.g., 612a) of the flow control assembly 610 can be fixed in place during or following placement of the flow control assembly 610 in the chamber. Fixation of an anchor element may constrain movement of the anchor element such that, during operation, the flow control assembly 610 remains in a locked configuration. For example, fixation of an anchor element may maintain an overall (e.g., combined) length of actuation elements for a flow control element, during operation. In some embodiments, fixation of anchor element(s) is done at substantially the same time as the locking elements are placed into a locked configuration. In some embodiments, fixation of anchor element(s) is done following placement of the locking elements into a locked configuration. Anchor elements may be fixed to the outer membrane 615 via a bonding, a friction fit, an interference fit, or other suitable attachment mechanism. FIG. 6 further illustrates a cross-section view taken along the axis indicated by B-B and that depicts embodiments of anchor element fixation. In a first embodiment 620, an anchor element portion 612a is fixed to an outer membrane portion 615 by a keying into a groove. In a second embodiment 630, an anchor element portion 612a is fixed to an outer membrane portion 615 by a friction fit.

According to some embodiments of the present disclosure, each flow control element 611 is positioned for actuation along a given actuation axis (e.g., 618). The actuation axis may be such that, during actuation of an actuation element 614 of an individual flow control element 611, a corresponding gating element 616 of the actuated flow control element 611 is moved in a path that is substantially parallel to the given actuation axis. In some embodiments, at least two flow control elements 611 are actuated along a same actuation axis. In some embodiments, at least two flow control elements 611 are actuated along actuation axes that are different. In the example of FIG. 6, two actuation axes are positioned at an angle 613 with respect to one another. In some embodiments, a first actuation axis can be positioned at angle with respect to a second actuation axis that is about 10 degrees, about 60 degrees, about 90 degrees, about 120 degrees, about 180 degrees, about 220 degrees, about 270 degrees, about 310 degrees, or about 350 degrees. The first actuation axis can be positioned at angle with respect to a second actuation axis that is between any of the aforementioned angles. In some embodiments, a plurality of flow control elements 611 have corresponding actuation axes that are arranged about a collection region of a drainage element. The flow control elements 611 can be arranged in a (geometric) pattern. The arrangement can comprise a plurality of sides that correspond to an actuation axis of at least one flow control element 611. In some embodiments, the flow control elements 611 can be arranged in a generally triangular, rectangular, pentagonal, or hexagonal arrangement. In some embodiments, anchoring elements are generally linear in shape. In some embodiments, anchoring elements comprise one or more curves or bends. In FIG. 6, for example, the anchoring element comprises a bend having a bend angle 617. In some embodiments, a curve and/or a bend in the anchoring element provides a coupling arrangement for two adjacent flow control elements 611 that have differing actuation axes.

Figure 7:
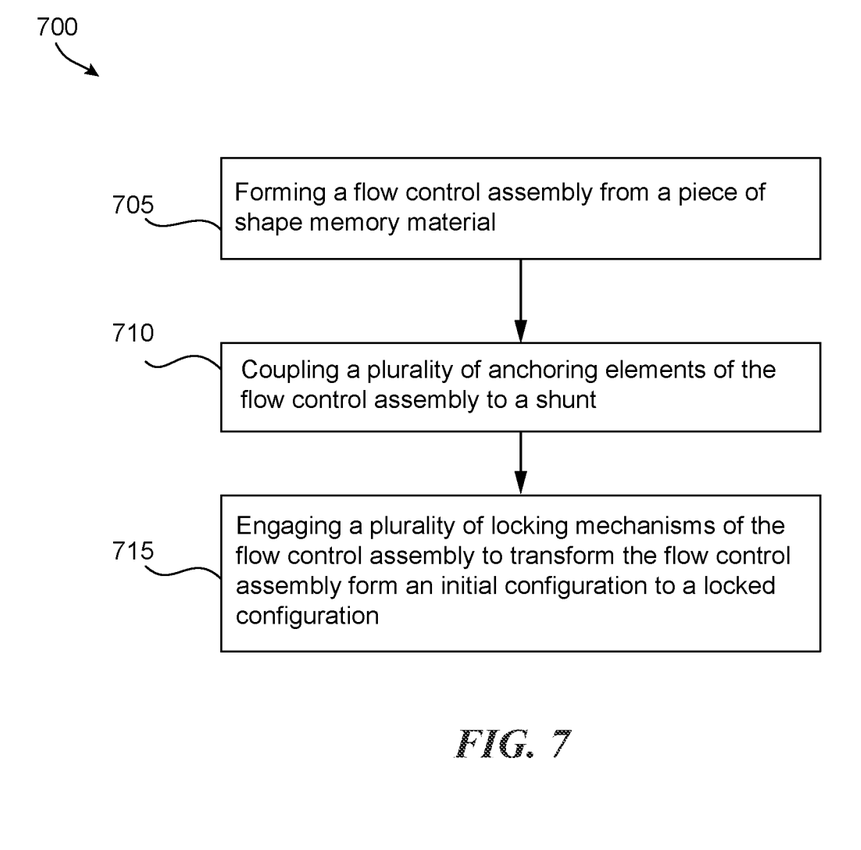
FIG. 7 is a flow chart depicting a method of manufacturing an adjustable shunt in accordance with an embodiment of the present technology.

Referring now to FIG. 7, a method 700 of manufacturing an adjustable shunt that includes several operations is depicted. A first operation 705 includes forming a flow control assembly from a piece of shape memory material, such as a piece (e.g., sheet, tube, etc.) of nitinol. In some embodiments, operation 705 includes forming the flow control assembly to have a plurality of anchoring elements, a plurality of locking mechanisms, and a plurality of flow control elements. Each flow control element is formed to include a first actuation element, a second actuation element, and a gating element that is disposed between the first and second actuation elements. A second operation 710 includes coupling the plurality of anchoring elements to the shunt. A third operation 715 includes engaging the plurality of locking mechanisms to transform the flow control assembly from an initial (e.g., fabricated) state or configuration to a locked state or configuration. According to some embodiments, in the locked configuration at least one of the first and second actuation elements are placed into a strained configuration (e.g., deformed relative to their preferred/fabricated geometric configurations) such that the flow control assembly is positioned to at least partially control flow of fluid through a shunt. For example, the first and second actuation elements can be placed into a biased configuration, as described herein above.

Examples

Several aspects of the present technology are set forth in the following examples:
1. An adjustable shunt, comprising:
   a drainage element having a first end portion positionable within a first body region, a second end portion positionable within a second body region, and a lumen fluidly coupling the first end portion and the second end portion, wherein the first end portion includes a first port and a second port;
   a first flow control element configured to control the flow of fluid through the first port, wherein the first flow control element includes a first gating element moveable along a first actuation axis; and a second flow control element configured to control the flow of fluid through the second port, wherein the second flow control element includes a second gating element moveable along a second actuation axis, wherein the first actuation axis is not parallel to the second actuation axis.

2. The adjustable shunt of example 1 wherein the first actuation axis is disposed at an angle from about 10 degrees to about 310 degrees relative to the second actuation axis.

3. The adjustable shunt of examples 1 and 2 wherein the first flow control element and the second flow control element are disposed about a collection region configured to receive fluid entering the drainage element via the first port and/or the second port.

4. The adjustable shunt of any of examples 1-3 wherein the drainage element further includes a third port at the first end portion, and wherein the adjustable shunt further comprises:

a third flow control element configured to control the flow of fluid through the third port, wherein the third flow control element includes a third gating element moveable along a third actuation axis, wherein the third actuation axis is not parallel to the first actuation axis or the second actuation axis.

5. The adjustable shunt of example 4 wherein the first flow control element, the second flow control element and the third flow control element are arranged in a triangular configuration.

6. The adjustable shunt of any of examples 1.5 wherein:

the first flow control element includes a first actuation element and a first locking mechanism that, when in a locked configuration, at last partially deforms the first actuation element relative to its preferred geometry; and the second flow control element includes a second actuation element and a second locking mechanism that, when in a locked configuration, at least partially deforms the second actuation element relative to its preferred geometry.

7. The adjustable shunt of example 6 wherein:

the first flow control element includes one or more first anchors, wherein the first locking mechanism is integrally formed with the one or more first anchors; and the second flow control element includes one or more second anchors, wherein the second locking mechanism is integrally formed with the one or more second anchors.

8. the adjustable shunt of any of examples 1-7 wherein the first gating element is configured to change a fluid resistance through the first port upon actuation of the first flow control element, and wherein the second gating element is configured to change a fluid resistance through the second port upon actuation of the second flow control element.

9. The adjustable shunt of any of examples 1-8 wherein the first port and the second port have a different size and/or shape.

10. The adjustable shunt of any of examples 1-9 wherein the first body region is the anterior chamber of a patient's eye and the second body region is a target outflow location.

11. A flow control assembly for modification of flow in an adjustable intraocular shunt, comprising:

a plurality of anchoring elements;

a plurality of non-linearly arranged flow control elements coupled to the plurality of anchoring elements, wherein each flow control element comprises a first actuation element, a second actuation element, and a gating element disposed therebetween; and a plurality of locking mechanisms coupled to the plurality of anchoring elements and the plurality of non-linearly arranged flow control elements, wherein the plurality of locking mechanisms, when in a locked position, at least partially deform the first actuation element and/or the second actuation element of the plurality of non-linearly arranged flow control elements relative to their preferred geometries.

12. The flow control assembly of example 11 wherein the plurality of locking mechanisms are integrally formed with the plurality of anchoring elements.

13. The flow control assembly of examples 11 or 12 wherein a first anchoring element is shared by the first flow control element and the second flow control element.

14. The flow control assembly of example 13 wherein a second anchoring element is shared by the second flow control element and a third flow control element.

15. The flow control assembly of any of examples 11-14 wherein an end of a first flow control element is coupled with a beginning of a second flow control element.

16. The flow control assembly of any of examples 11-15 wherein each flow control element is shaped and sized for movement along a given actuation axis.

17. The flow control assembly of example 16 wherein the actuation axes of the plurality of flow control elements are disposed at an angle from about 11 degrees to about 310 degrees with respect to one another.

18. The flow control assembly of example 17 wherein the plurality of flow control elements are arranged along actuation axes that generally correspond to a triangular, rectangular, pentagonal, or hexagonal arrangement.

19. The flow control assembly of any of examples 11-18 wherein at least one anchoring element of the plurality of anchoring elements includes a bent region such that it is non-linear.

20. The flow control assembly of any of examples 11-19 wherein the flow control assembly is coupled with a shunt having a plurality of flow ports, and wherein the flow control elements are positioned for modifying flow through the plurality of flow ports.

21. A method of manufacturing an adjustable shunt having a shunt and a flow control assembly, the method comprising:

forming the flow control assembly from a piece of shape memory material, the flow control assembly having a plurality of anchoring elements, a plurality of locking mechanisms, and a plurality of flow control elements, wherein each flow control element comprises a first actuation element, a second actuation element, and a gating element disposed therebetween;

coupling the plurality of anchoring elements to the shunt; and engaging the plurality of locking mechanisms to transform the flow control assembly from an initial configuration to a locked configuration, wherein, in the locked configuration, the first and second actuation elements are each placed into a strained state such that the flow control assembly is positioned to at least partially control the flow of fluid through the shunt.

22. The method of example 21 wherein the shunt includes a bladder, and wherein coupling the plurality of anchoring elements to the shunt comprises positioning the plurality of anchoring elements within the bladder.

23. The method of examples 21 or 22 wherein engaging the plurality of locking mechanisms is simultaneous with coupling the plurality of anchoring elements to the shunt.

24. The method of any of examples 21-23 wherein each locking mechanism comprises a locking feature and a retention feature, and wherein the engaging comprises coupling the locking feature and the retention feature.

25. The method of any of examples 21-24 wherein each flow control element is formed to be strained along a given actuation axis.

26. The method of example 25 wherein at least two actuation axes are formed at different angles.

27. The method of any of examples 21-26 wherein forming the flow control assembly includes forming the plurality of flow control elements to be integral with the plurality of anchoring elements.

28. The method of any of examples 21-27 wherein forming the flow control assembly includes laser cutting the flow control assembly from a piece of nitinol.

29. The method of any of examples 21-28 wherein the flow control assembly is cut from a single piece of nitinol.

30. A method of treating glaucoma, the method comprising:
draining aqueous from an anterior chamber of an eye to a target outflow location using an adjustable shunt, wherein the adjustable shunt includes (i) a plurality of inflow ports positioned within the anterior chamber and (ii) a flow control assembly having a plurality of individually actuatable flow control elements,
wherein each actuatable flow control element is shaped and sized for moving along a given actuation axis for modifying a flow resistance of individual ports of the plurality of inflow ports, and wherein, for at least two flow control elements, moving is along different actuation axes; and
adjusting the drainage rate of the aqueous by actuating at least one of the individually actuatable flow control elements.

31. The method of example 30, further comprising (i) actuating a first actuatable flow control element for moving along a first actuation axis, and (ii) actuating a second actuatable flow control element for moving along a second actuation axis that is at an angle with respect to the first actuation axis.

32. The method of example 31, further comprising (iii) actuating a third actuatable flow control element for moving along a third actuation axis that is at an angle with respect to the first actuation axis and the second actuation axis.

33. The method of example 32 wherein at least two of operations (i)-(iii) are performed at different times.

34. The method of any of examples 30-33 wherein adjusting the drainage rate includes blocking and/or unblocking the individual ports.

35. The method of any of examples 30-33 wherein actuating at least one of the individually actuatable flow control elements comprises applying energy to at least one of the individually actuatable flow control elements.

36. The method of example 35 wherein applying energy to the at least one of the individually actuatable flow control elements includes applying the energy non-invasively.

37. The method of example 36 wherein the energy includes laser energy.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the intraocular shunts described herein may be combined with any of the features of the other intraocular shunts described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions associated with intraocular shunts have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of manufacturing an adjustable shunt having a shunt and a flow control assembly, the method comprising:
forming the flow control assembly from a piece of shape memory material, the flow control assembly having a plurality of anchoring elements, a plurality of locking mechanisms, and a plurality of flow control elements, wherein each flow control element comprises a first actuation element, a second actuation element, and a gating element disposed therebetween;
coupling the plurality of anchoring elements to the shunt; and
engaging the plurality of locking mechanisms to transform the flow control assembly from an initial configuration to a locked configuration, wherein, in the locked configuration, the first and second actuation elements are each placed into a strained state such that the flow control assembly is positioned to at least partially control the flow of fluid through the shunt.

2. The method of claim 1 wherein the shunt includes a bladder, and wherein coupling the plurality of anchoring elements to the shunt comprises positioning the plurality of anchoring elements within the bladder.

3. The method of claim 1 wherein engaging the plurality of locking mechanisms is simultaneous with coupling the plurality of anchoring elements to the shunt.

4. The method of claim 1 wherein each locking mechanism comprises a locking feature and a retention feature, and wherein the engaging comprises coupling the locking feature and the retention feature.

5. The method of claim 1 wherein each flow control element is formed to be strained along a given actuation axis.

6. The method of claim 5 wherein at least two actuation axes are formed at different angles.

7. The method of claim 1 wherein forming the flow control assembly includes forming the plurality of flow control elements to be integral with the plurality of anchoring elements.

8. The method of claim 1 wherein forming the flow control assembly includes laser cutting the flow control assembly from a piece of nitinol.

9. The method of claim 1 wherein the flow control assembly is cut from a single piece of nitinol.

* * * * *